United States Patent [19]

Sugiyama et al.

[11] Patent Number: 4,739,261

[45] Date of Patent: Apr. 19, 1988

[54] FLAW SIZE MEASUREMENT EQUIPMENT USING EDDY CURRENTS

[75] Inventors: Sakae Sugiyama, Toukai; Akira Kobana, Hitachi; Makoto Senoh, Toukai, all of Japan

[73] Assignee: Hitachi, Ltd., Tokyo, Japan

[21] Appl. No.: 787,485

[22] Filed: Oct. 15, 1985

[30] Foreign Application Priority Data

Oct. 15, 1984 [JP] Japan ............................ 59-214371

[51] Int. Cl.$^4$ ...................... G01N 27/72; G01R 33/12
[52] U.S. Cl. ................................ 324/232; 324/227; 324/238
[58] Field of Search ............... 324/225, 226, 227, 237, 324/238, 240, 202, 232; 364/481, 550, 551

[56] References Cited

U.S. PATENT DOCUMENTS 4,628,261 12/1986 Hüschelrath et al. .............. 324/240

Primary Examiner—Reinhard J. Eisenzopf
Assistant Examiner—Walter E. Snow
Attorney, Agent, or Firm—Fay, Sharpe, Beall, Fagan, Minnich & McKee

[57] ABSTRACT

Equipment to measure flaws in an object using an eddy current. According to this equipment, attention is given to a relation between the amplitude of signal detected when the eddy current probe is scanning and the position of the eddy current probe, and the size of flaw is measured based upon the fact that scan distance of probe in which flaw detection signals of greater than a predetermined threshold value are obtained, is subject to change depending upon the depth of penetration of eddy current.

20 Claims, 7 Drawing Sheets

FLAW SIZE MEASUREMENT EQUIPMENT USING EDDY CURRENTS

BACKGROUND OF THE INVENTION

The present invention relates to non-destructive diagnostic equipment, and particularly to eddy current diagnostic equipment which is suited for measuring thickness, for detecting flaws and for measuring the size of flaws in structures such as conduits.

An eddy current method has been extensively used to non-destructively inspect metallic materials, and the state of the art is now such that flaws can be precisely measured. The conventional method of precisely measuring flaws based upon the phase method has been announced in the journal Mitsubishi Jyuko Giho entitled "Eddy Current Flaw Detecting Technique for Heat Conducting Pipes", Vol. 13, No. 3, May 1976, pp. 33-39.

With this method, the phase of flaw detection signal changes depending upon the depth of the flaw and the ratio relative to the whole thickness, whereby the size of the flaw is measured. This method can be effectively adapted when the shape of flaw does not change, but is not effective for detecting flaws of a variety of shapes such as cracks in an object, since the phase does not change linearly in such cases.

SUMMARY OF THE INVENTION

The object of the present invention is to provide equipment which is capable of precisely measuring the thickness and flaws of an object relying upon the eddy current method.

According to the present invention, the size of flaw is measured by considering the relation between the amplitude of signals detected when an eddy current probe is being scanned and the position of the eddy current probe, and by utilizing the fact that the scanning distance of the probe for producing flaw detection signals of greater than a predetermined value varies with the depth of penetration of eddy current.

DESCRIPTION OF THE PREFERRED EMBODIMENTS

The logical background of the present invention will be described below, first, in conjunction with FIGS. 1 to 4, prior to explaining the present invention.

The present invention is based upon the phenomenon that the half-value width of signals being detected by an eddy current scanning probe changes with the depth of penetration of eddy current, thereby enabling precise measurement of the thickness of the object and the dimensions of the flaw.

Figure 1:
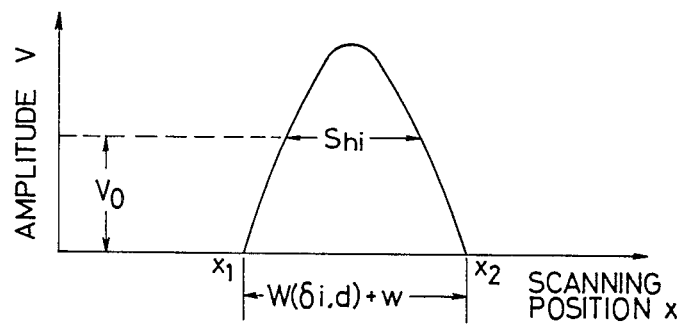
FIGS. 1 to 4 are diagrams explaining the principle of the present invention.
Figure 1:
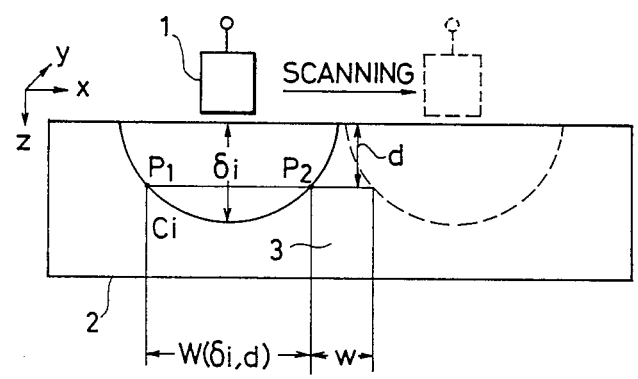

FIG. 1 shows schematically measurement of a flaw based upon the half-value width. In other words, FIG. 1 shows the relation between the scanning position x of the eddy current probe 1 and the amplitude V of the flaw detection signal. If explained using a coordinate (x, z) to simplify the description, the flaw 3 in the object 2 has a width w and is located at a position of a depth d from the surface of the object 2. Described below is a principle of the invention to measure the size of the flaw 3.

That is, if a coil excited by an AC current is brought close to a conductor which is an object, an eddy current is generated in the conductor due to electromagnetic induction. The intensity of eddy current varies with the surface conditions, magnetic properties and electric properties of the object. According to the eddy current flaw detecting method, the change in the intensity of eddy current is detected as the change of impedance of a coil thereby to measure the flaw and properties of the object (Hideyuki Ito et al., Electromagnetic Induction Testing, Handbook of Non-destructive Inspection, Chapter 5, published by Nikkan Kogyo Shimbunsha, 1978).

Referring to FIG. 1, if the probe 1 is scanned, the amplitude V of flaw detection signal starts to change from the position $x_1$, i.e., increases and then decreases and returns to the initial balanced value. Here, the amplitude V varies because of the reasons described below. That is, equilibrium has been so accomplished that the amplitude V becomes 0 when the probe 1 is placed on an object 2 that contains no flaw, the probe 1 then scans. Here, however, equilibrium is lost as the probe 1 approaches the flaw 3, and the amplitude V which is equivalent to an unbalanced signal increases. Therefore, the unbalanced condition peaks when the probe 1 scans directly over the flaw 3, and the amplitude V peaks. As the probe 1 moves away from the position just over the flaw 3, the amplitude V decreases and equilibrium is restored where the amplitude V is 0.

Here, the scan distance $Sh_i$ in which the amplitude V is greater than a predetermined value $V_0$, is affected by the depth $\delta_i$ of penetration of the eddy current, the depth d of the flaw 3 and the width w thereof. Namely, the scan distance $Sh_i$ is given by the equation (1), $$Sh_i = a[W(\delta_i, d) + w] \qquad (1)$$

where,

W is the distance between points $P_1$ and $P_2$ when the boundary $C_i$ of eddy current distribution comes into contact with the flaw, a is a constant determined by a predetermined value $V_0$.

The predetermined value $V_0$ may be experimentally found from a relation S/N of the measuring system, or may be set to a value that is smaller than a maximum amplitude by a predetermined ratio, or may be set to a value that is larger than the initial balanced value by a predetermined ratio.

Here, if the distribution C of eddy current or the depth $\delta$ of penetration is changed depending upon the frequency f for exciting the probe 1 or the intensity H of DC magnetic field applied to the object 2, another scan distance $Sh_j$ is obtained for the same flaw. The scan distance, in this case, is given by the following equation (2), $$Sh_j = a[W(\delta_j, d) + w] \qquad (2)$$

Further, if the width w is eliminated from the equations (1) and (2), the following equation is obtained (3)

$$\Delta Sh = a[W(\delta_i, d) - W(\delta_j, d)] \quad (3)$$

where,

ΔSh: difference in the moving distance.

Figure 2:
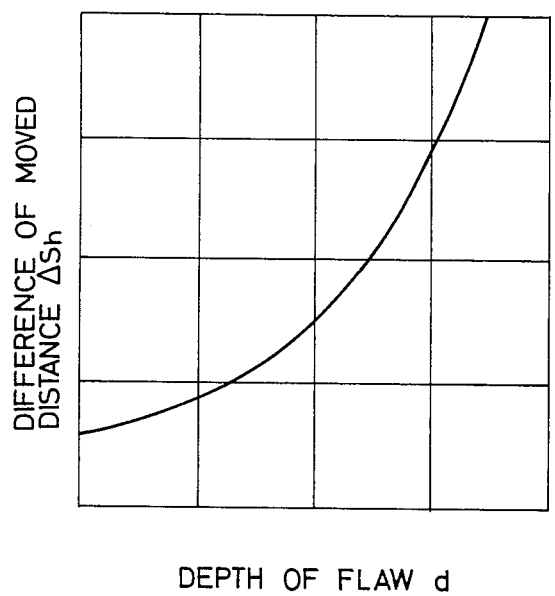

Therefore, if calibration curves are prepared in advance by experimentally or theoretically finding relations between the difference ΔSh of scan distance and the depth d of flaw, the depth of flaw can be obtained from the difference ΔSh of scan distance when an unknown flaw is inspected. FIG. 2 shows a calibration curve which experimentally demonstrates the fact that the difference ΔSh of moving distance for the depth of flaw can be represented by a single curve even when the flaw has a different width w.

It has been pointed out that the depth δ of penetration of eddy current can be changed depending upon the excitation frequency f or the DC magnetic field intensity H for the object. The reason is obvious from the widely known equation (4), $$\delta = (\pi f \mu \sigma)^{-\frac{1}{2}} \quad (4)$$

where,

δ: depth of penetration of eddy current,
μ: permeability of the object,
σ: conductivity of the object,
f: excitation frequency.

Permeability μ of the object apparently changes depending upon the DC magnetic field intensity H applied from the external side. For instance, the permeability μ decreases with the increase in the DC magnetic field intensity H. Therefore, the depth δ of penetration changes depending upon the excitation frequency f or the DC magnetic field intensity H.

Figure 3:
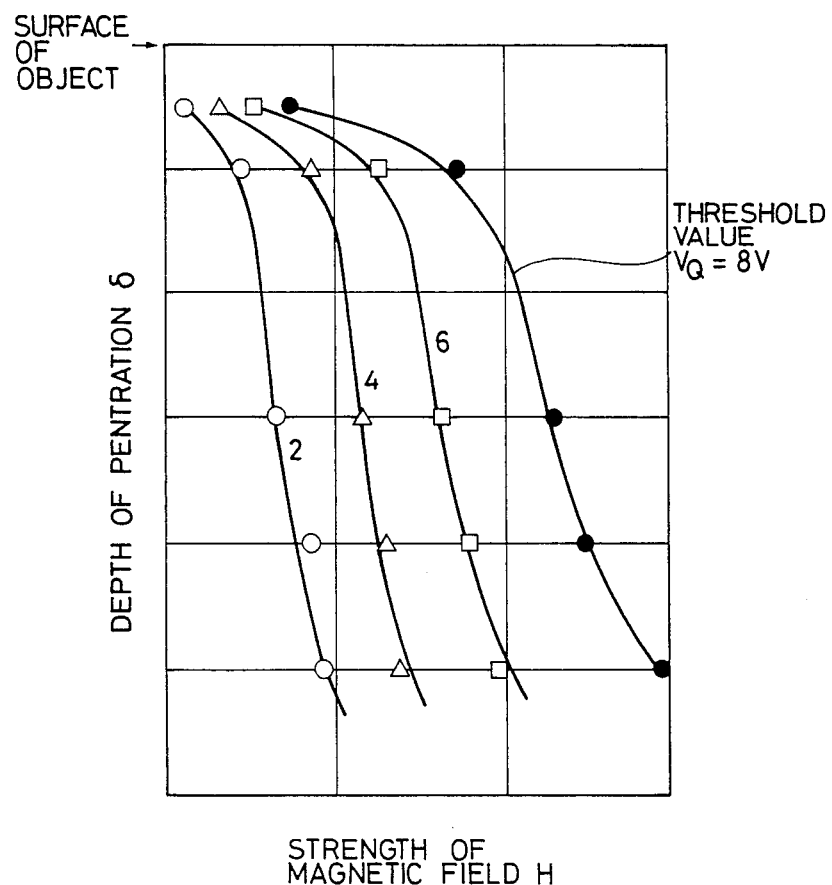

FIG. 3 shows relations between the DC magnetic field intensity H and the depth δ of penetration of eddy current, wherein the parameter is the aforementioned threshold value $V_0$ set for the amplitude of flaw detection signal. It will be understood that as the threshold value $V_0$ is set high, the magnetic field intensity H must be increased to increase the depth δ of penetration.

The depth d of flaw is measured as described above. An explanation is given below on how to find the width w of flaw. It hs been explained that the scan distance Sh of eddy current probe changes depending upon the depth d and width w of flaw when the depth δ of penetration of eddy current is maintained constant. From the equation (1), it is obvious that the width w of flaw is found as given by the following equation (5), $$w = Shi/a - W(\delta_i, d) \quad (5)$$

The first term on the right side of the equation (5) can be measured. The second term can also be found by calculation from a calibration curve that is obtained relying upon known flaws. Thus, the width w of the flaw can be found.

Figure 4:
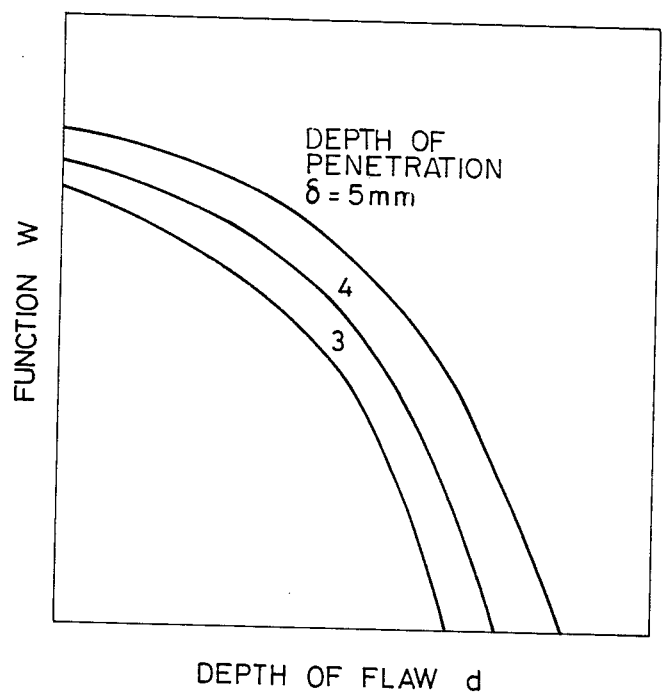

FIG. 4 shows simulated results of eddy current distribution as an example of the function $W(\delta_i, d)$. It will be understood that the depth δ of penetration of eddy current is determined by the excitation frequency f or the DC magnetic field intensity H, and the function W is found from the depth d that was found previously.

In the above description, the eddy current probe scans the direction of the x axis in FIG. 1. However, even when the eddy current probe scans in the direction of y-axis, the width of flaw can also be found in the direction of y-axis.

Figure 5:
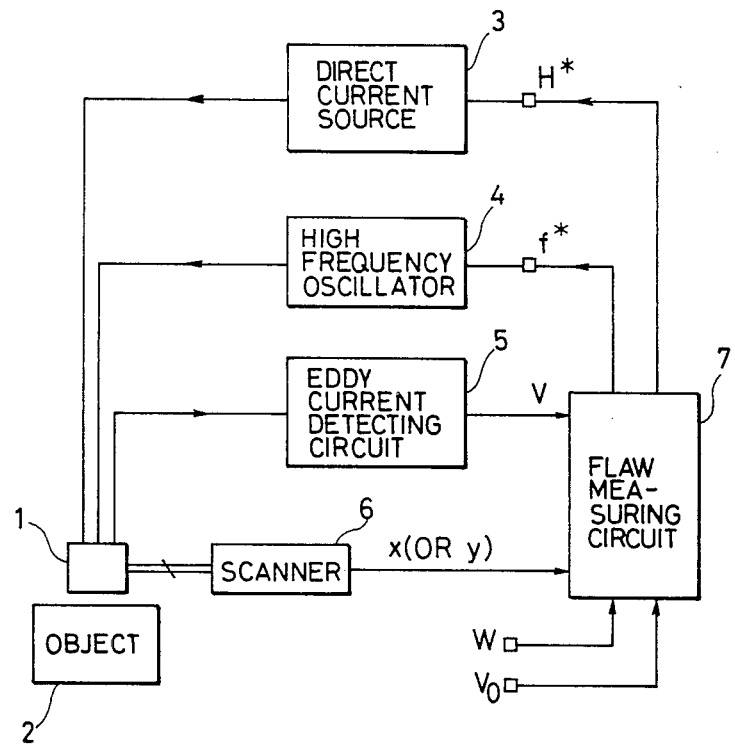
FIG. 5 is a block diagram illustrating an embodiment of the present invention.

In the foregoing paragraphs were described the theoretical background and principle of the invention. Next, equipment required for invention will be described. FIG. 5 shows the structure of eddy current diagnostic equipment of the present invention for calculating the size (depth, width, length) of flaw from the difference of moving distance of the eddy current probe.

A direct current is supplied from a direct current source 3 to the eddy current probe 1, and a high-frequency current is supplied from a high-frequency oscillator 4 to the eddy current probe 1, so that the object 2 is DC magnetized and an eddy current penetrates thereinto. An eddy current detecting circuit 5 detects the eddy current in the object 2 via the eddy current probe 1 that is mechanically coupled to a scanner 6, and sends the amplitude V of flaw detection signal, which is a detected result, to a flaw measuring circuit 7 of the next stage. The flaw measuring circuit 7 calculates the depth d and width w of flaw in the object 2 upon receipt of the amplitude V and a probe position signal x (or y) from the scanner 6 and based further upon the aforementioned function W and the threshold value $V_0$ that have been input in advance. The flaw measuring circuit 7 feeds a desired excitation frequency f* and a desired DC magnetic field intensity H* that are necessary for calculating the depth and width of flaw, back to the high-frequency oscillator 4 and to the direct current source 3. Here, the eddy current probe 1 may be an ordinary one using a high-frequency coil, or may be of the structure which is further equipped with a DC magnetization coil. Further, the eddy current probe 1, direct current source 3, high-frequency oscillator 4, eddy current detecting circuit 5 and scanner 6 may be those that operate as described above, and the existing devices can be utilized. However, the direct current source 3 and the high-frequency oscillator 4 must be provided with external terminals to introduce the desired DC magnetic field intensity H* and the desired excitation frequency f*, respectively.

Figure 6:
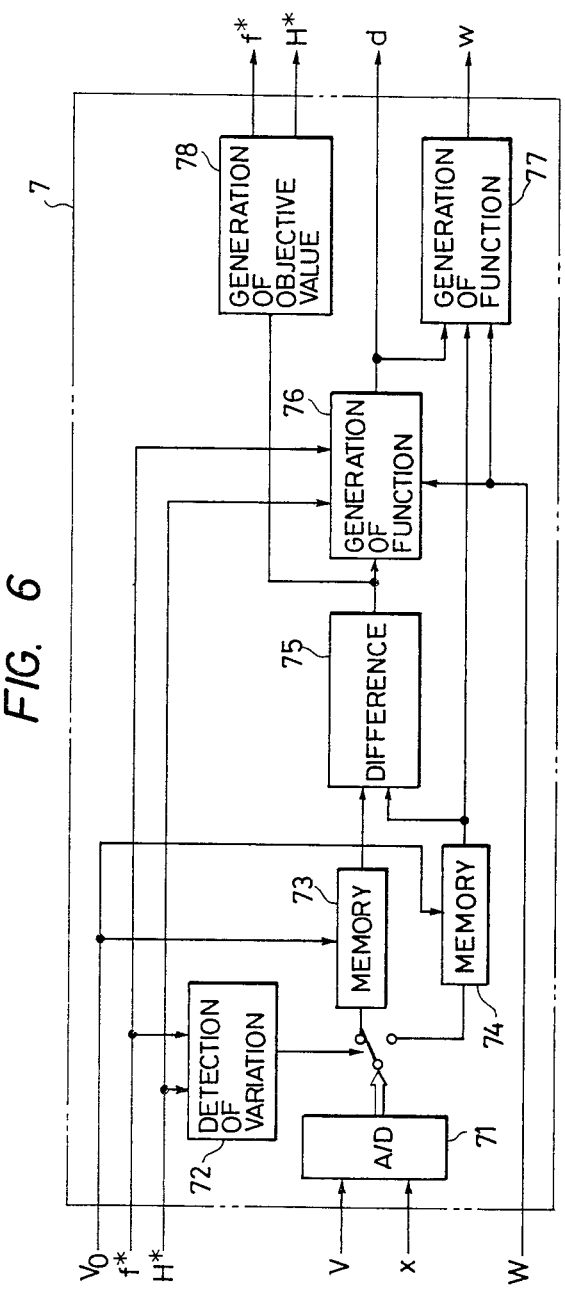
FIG. 6 is a diagram showing a constitution of the flaw measuring circuit of FIG. 5.
Figure 7:
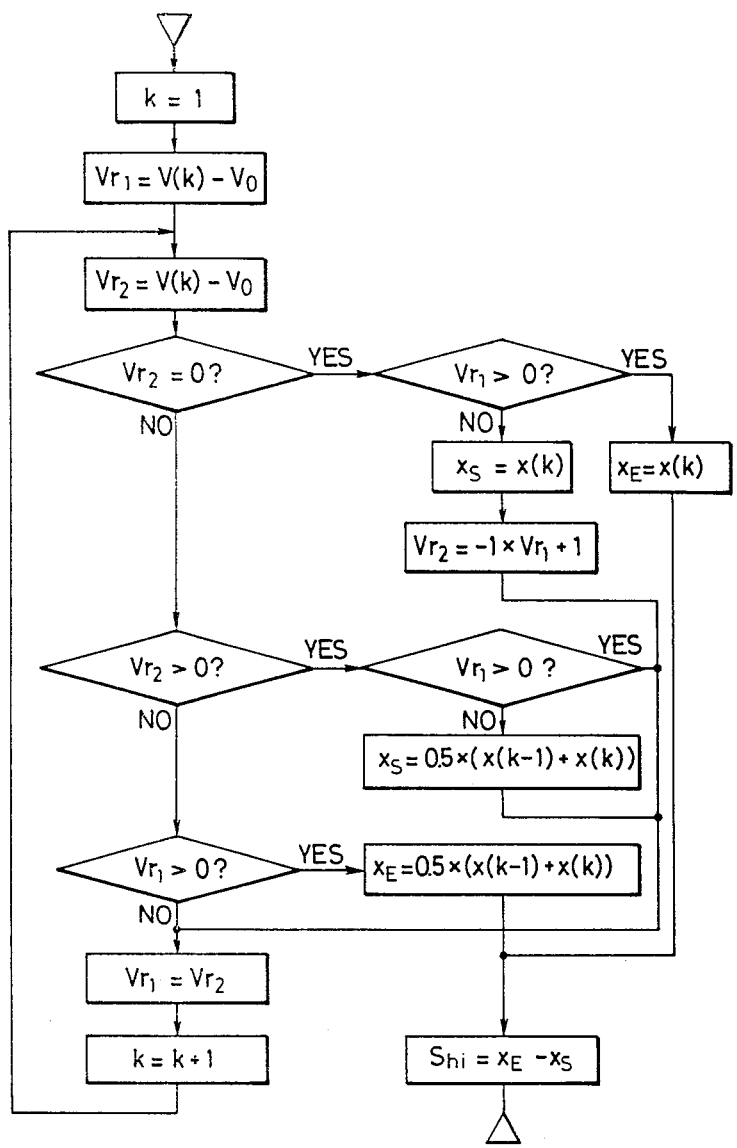
FIG. 7 is a flow chart for finding the scan distance with the distance measuring circuit, which is equipped with a memory.

FIG. 6 shows a structure of the flaw measuring circuit wherein the amplitude V of flaw detection signal from the eddy current detecting circuit 5 and the position signal x (or y) of eddy current probe 1 from the scanner 6 are alternately stored as a pair in the moving distance measuring circuits 73, 74 with memory via an A/D converter circuit 71. First, the amplitude V and position signal x are stored in the moving distance measuring circuit 73 with memory when the DC magnetic field intensity is Hi or the excitation frequency is $f_i$ and, then, the amplitude V and position signal x are stored in the scan distance measuring circuit 74 with memory when the DC magnetic field intensity is Hj or the excitation frequency is $f_j$. Thus, the amplitude V and position signal x are alternatingly stored in the scan distance measuring circuits 73, 74 with memory every time the DC magnetic field intensity H or the excitation frequency f is renewed. A change detecting circuit 72 switches the scan distance measuring circuits 73, 74 with memory when it is detected that either one of the desired value H* or f* is changed by renewal. Therefore, the scan distance measuring circuits 73, 74 with memory store the probe scanning position and the amplitude V obtained at the scanning position. Here, the scan distance measuring circuit 73, 74 with a memory refers to be threshold value $V_0$ set from an external unit to find probe moving distance Shi and Shj having amplitude V greater than the threshold value $V_0$ based upon the algorithm shown in FIG. 7.

The algorithm will be described below briefly. The algorithm finds a scanning position at which the amplitude V is greater than the threshold value $V_0$ and a scanning position at which the amplitude V is smaller than the threshold value $V_0$. Namely, an amplitude $V(k)$ at a k-th scanning position and a probe position $x(k)$ are read from the memory to find such a k that $V(k-1) < V_0 < V(k)$, and a scanning position $x_S$ at which the amplitude is greater than the threshold value $V_0$ is found from the following equation, $$x_S = [x(k-1)+x(k)] \cdot \tfrac{1}{2} \qquad (6)$$

However, when there exists such a k that $V(k)=V_0$ and $V(k-1) < V_0$, the scanning position is found according to the following equation, $$x_S = x(k) \qquad (7)$$

As for the scanning position $x_E$ at which the amplitude is smaller than the threshold value $V_0$, such a k is found as $V(k-1) > V_0 > V(k)$.

$$x_E = [x(k-1)+x(k)] \cdot \tfrac{1}{2} \qquad (8)$$

However, when there exists such a k that $V(k)=V_0$ and $V(k-1) > V_0$, the scanning position $x_E$ is found from the following equation, $$x_E = x(k) \qquad (9)$$

By finding a difference between $x_S$ and $x_E$, therefore, the moving distances Shi, Shj are found. A difference circuit 75 finds a difference between the moving distances Shi and Shj, and a difference $\Delta Sh$ which is found is given to a function generating circuit 76 with memory and to a desired value generating circuit 78. The function generating circuit 76 with memory is stores in advance a relation between the depth d of flaw and the difference $\Delta Sh$ of moving distance as shown, for example, in FIG. 2 with the excitation frequency or the DC magnetic field intensity as a parameter. Therefore, as a signal $\Delta Sh$ is input from the difference circuit 75, the function generating circuit 76 readily obtains the depth d of flaw with reference to the excitation frequency $f^*$ or the DC magnetic field intensity $H^*$. A function generating circuit 77 with memory stores a function W in advance to calculate the width W of flaw in accordance with the equation (5) with reference to the moving distance Shi (or Shj) and the depth d of flaw. When the difference $\Delta Sh$ of moving distance is smaller than a predetermined significant difference $\epsilon$, the desired value generating circuit 78 changes the desired excitation frequency $f^*$ or the desired DC magnetic field intensity $H^*$ linearly or incrementaly. For example, the excitation frequency f is incrementally changed according to the following equation, $$f_j^* = f_i + \Delta f \qquad (10)$$

where,
$f_i$: excitation frequency of the i-th scanning of the eddy current probe,
$f_j^*$: desired excitation frequency of the j-th scanning,
$\Delta f$: changing width of excitation frequency.

The changing width $\Delta f$ of excitation frequency is controlled until the difference $\Delta Sh$ of moving distance becomes larger than the significant difference $\epsilon$. Even when the DC magnetic field intensity is to be changed, the control operation is performed in the same manner as above in accordance with the equation (11). Here, symbols have the same meanings as those of the equation (10).

$$H_j^* = H_i + \Delta H \qquad (11)$$

Here, whether the excitation frequency f should be changed or the DC magnetic field intensity H should be changed, is easily determined. When the object 2 consists of a ferromagnetic material, both the excitation frequency f and the DC magnetic field intensity H may be changed, but giving priority to the latter. When the object 2 is not composed of a ferromagnetic material, only the excitation frequency f need be changed.

As mentioned above, the present invention makes it possible to easily and very precisely measure the size (depth, width, length) of flaws that could not be correctly measured with the existing eddy current method. Furthermore, the equipment of the present invention is simply constructed, and can be adapted to diagnosing structures and materials in a variety of fields relying upon the eddy current method.

We claim:
1. Flaw size measurement equipment using eddy currents, comprising:
an eddy current probe which generates eddy currents in an electrically conductive object and which applies a DC magnetic field to the object;
scanning means which causes said eddy current probe to scan the surface of the object;
a direct current source which supplies a direct current to said eddy current probe to generate the DC magnetic field;
high-frequency oscillating means which supplies a high-frequency excitation current to said eddy current probe to generate an AC magnetic field to cause the eddy currents in the object;
said eddy current probe causing first and second eddy current distributions in the object by changing at least one of the direct current supplied from said direct current source and the excitation frequency of high-frequency excitation current supplied from said high frequency oscillating means;
eddy current detecting means which detects first and second flaw detection signals corresponding respectively to first and second eddy current distributions in the object via said eddy current probe; and
flaw measuring means which finds first and second probe scanning distances in which respective first and second flaw detection signals of greater than a predetermined threshold value are obtained, relying upon the amplitude of the flaw detection signals obtained from said eddy current detecting means and upon probe scanning position signals from said scanning means while said eddy current probe is scanning, and which determines the size of a flaw in the object with reference to predetermined relationships among the first and second eddy current distributions, the first and second probe scanning distances and the depths and widths of flaws.

2. The flaw size measurement equipment using eddy current acording to claim 1, wherein said flaw measuring means measures the depth of the flaw relying upon the difference between the first probe scanning distance in the first eddy current distribution and the second probe scanning distance in the second eddy current distribution that is different from the first eddy current distribution with reference to predetermined relationships among differences between the first and second probe scanning distances and depths of flaws.

3. The flaw size measurement equipment using eddy currents according to claim 1, wherein the direct current supplied from said direct current source and the excitation frequency of high frequency excitation current supplied from said high frequency oscillating means are variably set under the control of said flaw measuring means for causing the first and second eddy current distributions in the object.

4. The flaw size measurement equipment using eddy current according to claim 2, wherein said flaw measuring means finds the width of the flaw from the depth of the flaw and one of the first and second probe scanning distances with reference to predetermined relationships between the depths of flaws and the eddy current distributions corresponding to said one of first and second probe scanning distances.

5. The flaw size measurement equipment using eddy currents according to claim 2, wherein said direct current source and said high-frequency oscillating means are controlled by said flaw measuring means until there appears a significant difference between the first and second probe scanning distances so as to change the direct current and the excitation frequency of high frequency excitation current supplied to said eddy current probe and to cause the second eddy current distribution to be substantially different from the first eddy current distribution.

6. The flaw size measurement equipment using eddy currents according to claim 4, wherein at least the depth of the flaw, the excitation frequency and the DC magnetic field are used as parameters to establish a relation beween the width of the flaw and the probe scanning distances.

7. The flaw size measurement equipment using eddy currents accordinng to claim 3, wherein said direct current source and said high-frequency oscillating means are controlled by said flaw measuring means until there appears a significant difference between the first and second probe scanning distances so as to change the direct current and the excitation frequency of high frequency excitation current supplied to said eddy current probe to cause the second eddy current distribution to be substantially different from the first eddy current distribution.

8. Flaw size measuring equipment using eddy currents, comprising:
  means for applying to an object a first unidirectional magnetic field exhibiting a magnetic field intensity within the object, and a second magnetic field alternating at a high frequency and causing eddy currents within the object;
  means for causing said applying means to scan the surface of the object and for providing location signals indicative of relative positions between said applying means and the object;
  means for detecting and providing detection signals representative of characteristics of said eddy current in the object; and
  flaw measuring means for causing changes in said intensity and said frequency to provide a plurality of said detection signals, for receiving said position and detection signals, for determining scanning distances at a first one of said intensity and frequency over which an amplitude of said detection signals exceeds a threshold value, for determining scanning distances at a second one of said intensity and frequency over which the amplitude exceeds the threshold value, and for determining the depths and widths of flaws on the basis of predetermined relations among differences in said scanning distances at said first and second ones of said intensities and frequencies and depths and widths of flaws.

9. The flaw size measuring equipment of claim 8, wherein said detecting means provides detection signals representative of the distribution of eddy currents along said scanning distances.

10. The flaw size measuring equipment of claim 8, wherein:
  said applying means causes said first and second magnetic fields corresponding to a first one of said scanning distances to provide eddy currents exhibiting a first depth of penetration into the object and said first and second magnetic fields corresponding to a second one of said scanning distances to provide eddy currents exhibiting a second and different depth of penetration, and
  said detecting means provides detection signals having values influenced by the depths of penetration.

11. The flaw size measuring equipment of claim 8:
  wherein said applying means causes said first and second magnetic fields corresponding to a first one of said scanning distances to provide eddy currents exhibiting a first distibution in the object and said first and second magnetic fields corresponding to a second one of said scanning distances to provide eddy currents exhibiting a second and different distribution; and
  said detecting means provides said detection signals having values influenced by said distributions of eddy currents.

12. The flaw size measurement equipment of claim 8, wherein said flaw measuring means measures the depths of flaws relying upon the difference between a first scanning distance corresponding to said first one of said intensity and frequency and a second scanning distance corresponding to said second one of said intensity and frequency with reference to predetermined relations among differences between the first and second scanning distances and depth of flaw.

13. Flaw size measuring equipment using eddy currents, comprising:
  means for applying to an object a first unidirectional magnetic field exhibiting a magnetic field intensity within the object, and a second magnetic field alternating at a high frequency and causing eddy currents within the object;
  means for causing said applying means to scan the object and for providing location signals indicative of relative positions between said applying means and the object;
  means for detecting and providing detection signals representative of characteristics of said eddy currents in the object; and
  flaw measuring means for causing changes in depth of penetration of said eddy currents into the object to provide a plurality of said detection signals, for receiving said position and detection signals, for determining scanning distances at a first depth of penetration by said eddy currents into the object over which an amplitude of said detection signals exceeds a threshold value, for determining scanning distances at a second and different depth of said penetration over which the amplitude exceeds the threshold value, and for determining the depths of flaws on the basis of predetermined relations among differences in said scanning distances at said first and second depths of penetration, and depths flaws.

14. The flaw size measuring equipment of claim 13, wherein said flaw measuring means includes means for changing said depths of penetration by varying one of said intensity and said frequency.

15. The flaw size measurement equipment of claim 13, wherein said flaw measuring means measures the depths of flaws by relying upon the difference between first scanning distances corresponding to the first depth of penetration and second scanning distances corresponding to the seccond depth of penetration with reference to predetermined relations among differences between the first and second scanning distances and depths of flaws.

16. The flaw size measurement equipment of claim 15, wherein said flaw measuring means finds the widths of flaws from the depths of flaws and one of the first and second scanning distances by reference to predetermined relations among depths of flaws and depths of penetration corresponding to said first and second scanning distances.

17. Flaw size measuring equipment using eddy currents, comprising:
means for applying to an object a first unidirectional magnetic field exhibiting a magnetic field intensity within the object, and a second magnetic field alternating at a high frequency and causing eddy curents within the object;
means for causing said applying means to scan the object and for providing location signals indicative of relative positions betwen said applying means and the object;
means for detecting and providing detection signals representative of characteristics of said eddy currents in the object; and
flaw measuring means for causing changes in distribution of eddy currents in the object to provide a plurality of said detection signals, for receiving said position and detection signals, for determining scanning distances with a first distribution of said eddy currents over which an amplitude of said detection signals exceeds a threshold value, for determining scanning distances with a second and different distribution of said eddy currents over which the amplitude exceeds the threshold value, and for determining the depths of flaws on the basis of predetermined relations among differences in said scanning distances corresponding to said first and second distributions of eddy currents and depths of flaws.

18. The flaw size measuring equipment of claim 17, wherein said flaw measuring means includes means for changing said distributions by varying one of said intensity and said frequency.

19. The flaw size measurement equipment of claim 17, wherein said flaw measuring means measures the depths of flaws by relying upon the difference between first scanning distances corresponding to the first distribution and second scanning distances corresponding to second distribution with reference to predetermined relations among differences between the first and second scanning distances and depths of flaws.

20. The flaw size measurement equipment of claim 19, wherein said flaw measuring means finds the widths of flaws from the depth of flaw and one of the first and second scanning distances by reference to predetermined relations amonng the depths of flaws and distributions corresponding to said first and second scanning distances.

* * * * *